US00PP29888P3

(12) United States Plant Patent
Wood

(10) Patent No.: US PP29,888 P3
(45) Date of Patent: Nov. 27, 2018

(54) ***VIBURNUM* PLANT NAMED 'SMNVODR'**

(50) Latin Name: *Viburnum opulus*
Varietal Denomination: SMNVODR

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 40 days.

(21) Appl. No.: 15/530,097

(22) Filed: Dec. 2, 2016

(65) Prior Publication Data

US 2018/0160594 P1 Jun. 7, 2018

(51) Int. Cl.
*A01H 5/12* (2018.01)
*A01H 5/02* (2018.01)

(52) U.S. Cl.
USPC ..... Plt./226
CPC ..... *A01H 5/02* (2013.01); *A01H 5/12* (2013.01)

(58) Field of Classification Search
USPC ..... Plt./226
See application file for complete search history.

*Primary Examiner* — Anne Marie Grunberg
(74) *Attorney, Agent, or Firm* — Cassandra Bright

(57) ABSTRACT

A new and distinct cultivar of *Viburnum* plant named 'SMNVODR' is disclosed, characterized by strong rusty red/orange new growth and bright yellow-green mature foliage. Plants are compact with strong basal branching with foliage resistant to leaf burn in the full sun. The new variety is a *Viburnum* plant normally produced as an outdoor garden or container plant.

6 Drawing Sheets

Latin name of the genus and species: *Viburnum opulus*.
Variety denomination: 'SMNVODR'.

BACKGROUND OF THE INVENTION

The present invention comprises a new and distinct variety of *Viburnum*, hereinafter referred to by the cultivar name 'SMNVODR'. This new *Viburnum* was developed through a breeding program in Grand Haven, Mich. 'SMNVODR' was selected from a population of seedlings grown from an open-pollinated including the seed parent *Viburnum opulus* 'Park Harvest', unpatented with a group of unnamed, unpatented *Viburnum opulus* pollinators. The open-pollination resulting in the new variety was conducted during 2008. Selection of the new variety was made during 2012.

The first asexual propagation of 'SMNVODR' was carried out Summer of 2012 by softwood cuttings at a commercial nursery in Grand Haven, Mich. 'SMNVODR' has been found to retain its distinctive characteristics through successive asexual propagations.

SUMMARY OF THE INVENTION

The following are the most outstanding and distinguishing characteristics of this new cultivar when grown under standard horticultural practices at a commercial nursery in Grand Haven, Mich.:

1. Compact plant form with a strong branching habit.
2. Resistance to leaf burn when planted in full sun.
3. Distinctive rusty red/orange new growth in Spring, and on new growth from a cutback.
4. Bright lime-yellow Summer foliage.

COMPARISON WITH KNOWN PARENT

'SMNVODR' is distinguished from its female parent *Viburnum* 'Park Harvest' in the following:

1. The new variety has good resistance to leaf burn, 'Park Harvest' foliage will burn in full sun.
2. Summer foliage of the parent variety is yellow, Summer foliage of the new variety is yellow-green.
3. Foliage color of the new variety is a deeper, stronger red/orange than that of 'Park Harvest'.

COMMERCIAL COMPARISON

'SMNVODR' is similar to the commercial variety *Viburnum* 'Roseum', unpatented, in most horticultural characteristics. 'SMNVODR' however differs in the following:

1. Plants of the new variety are shorter at maturity than plants of 'Roseum'.
2. Summer foliage of 'Roseum' is green, Summer foliage of the new variety is yellow-green.
3. Inflorescence type of the new variety is lace cap, 'Roseum' has a mop head inflorescence.

DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures. Plants were grown in Grand Haven, Mich.

Figure 1:
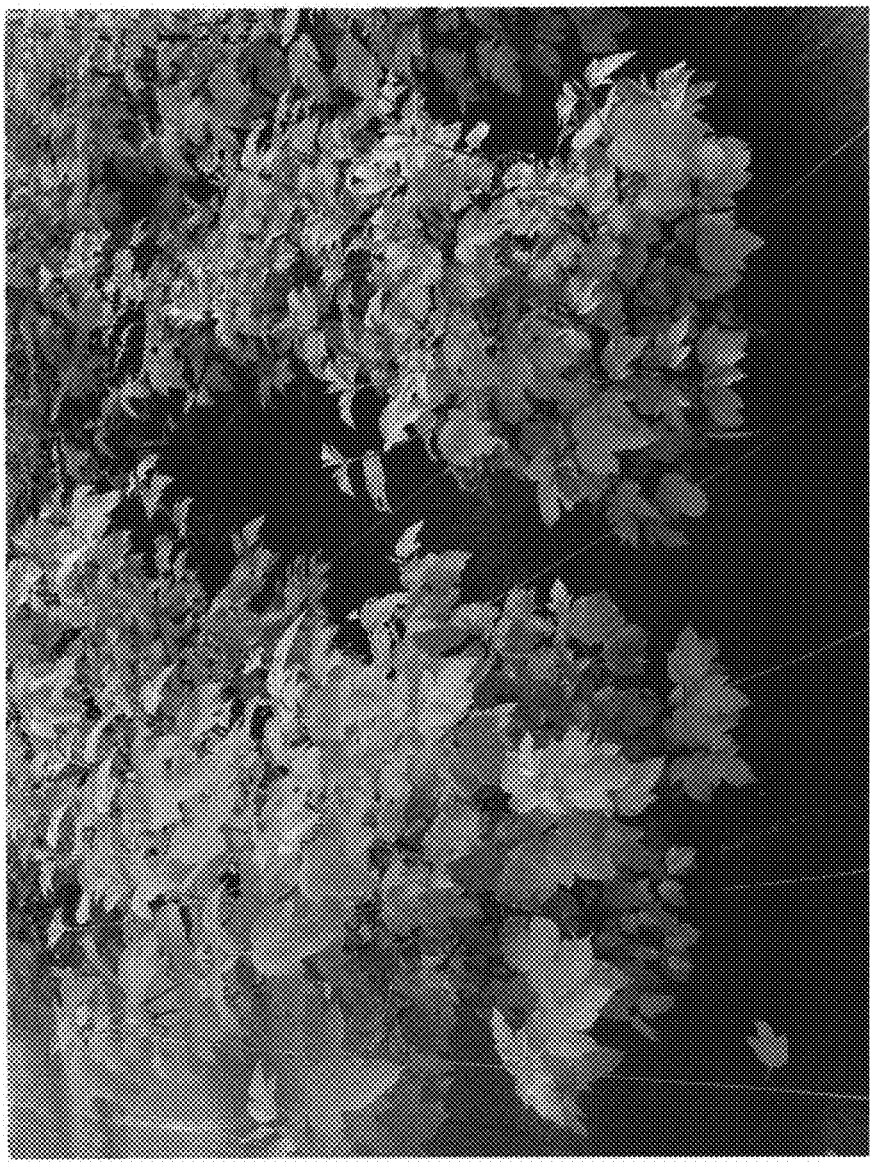

FIG. 1. Shows plants of 'SMNVODR' in 2 gallon containers at approximately 2 years old during Summer. The plant on the left in the photo shows typical yellow-green Summer foliage. The plant on the right in the photo shows red-/orange new growth after a cutback. Plants were grown in a polyhouse.

Figure 2:
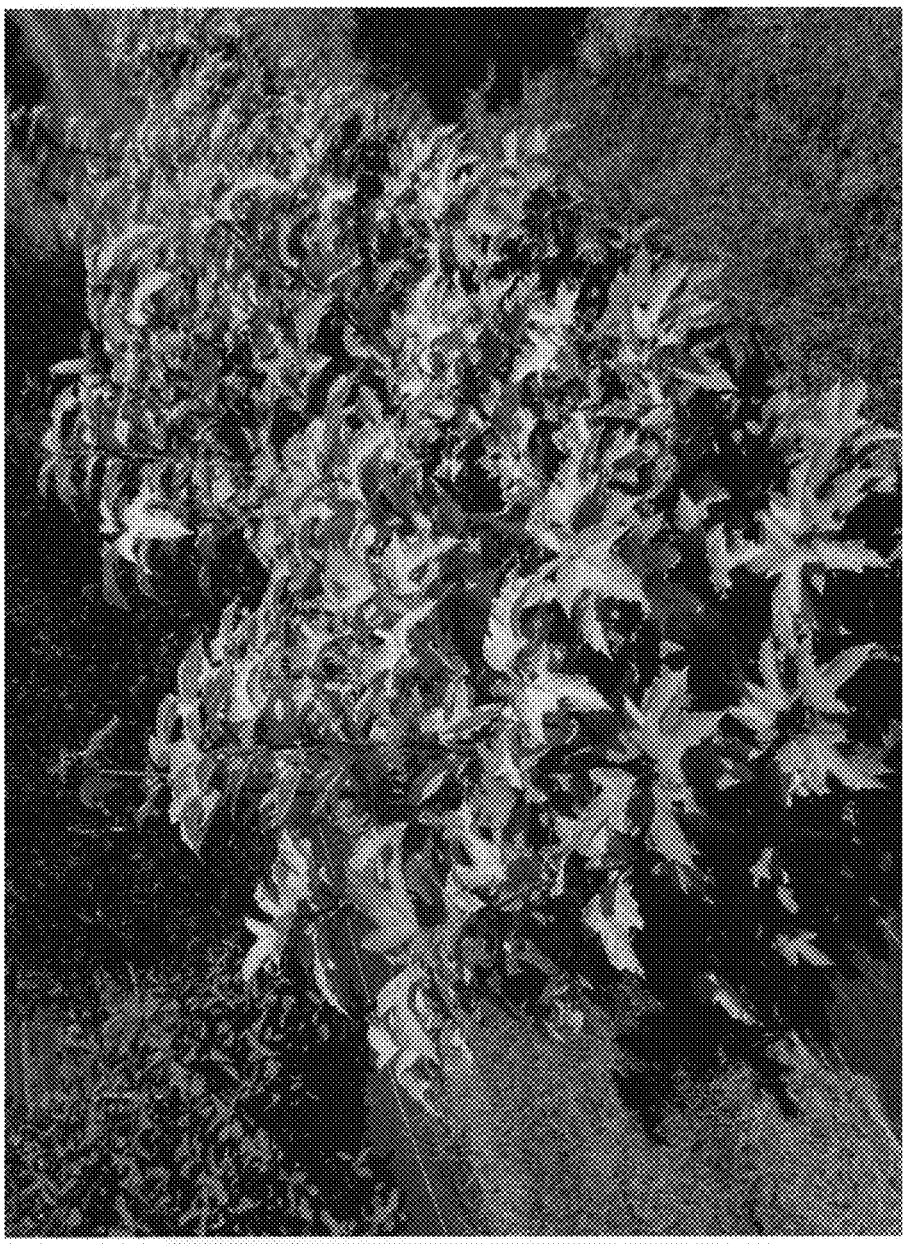

FIG. 2. Shows the overall plant habit of plants grown outdoors in Grand Haven, Mich. at approximately 3 years old, during Summer.

Figure 3:
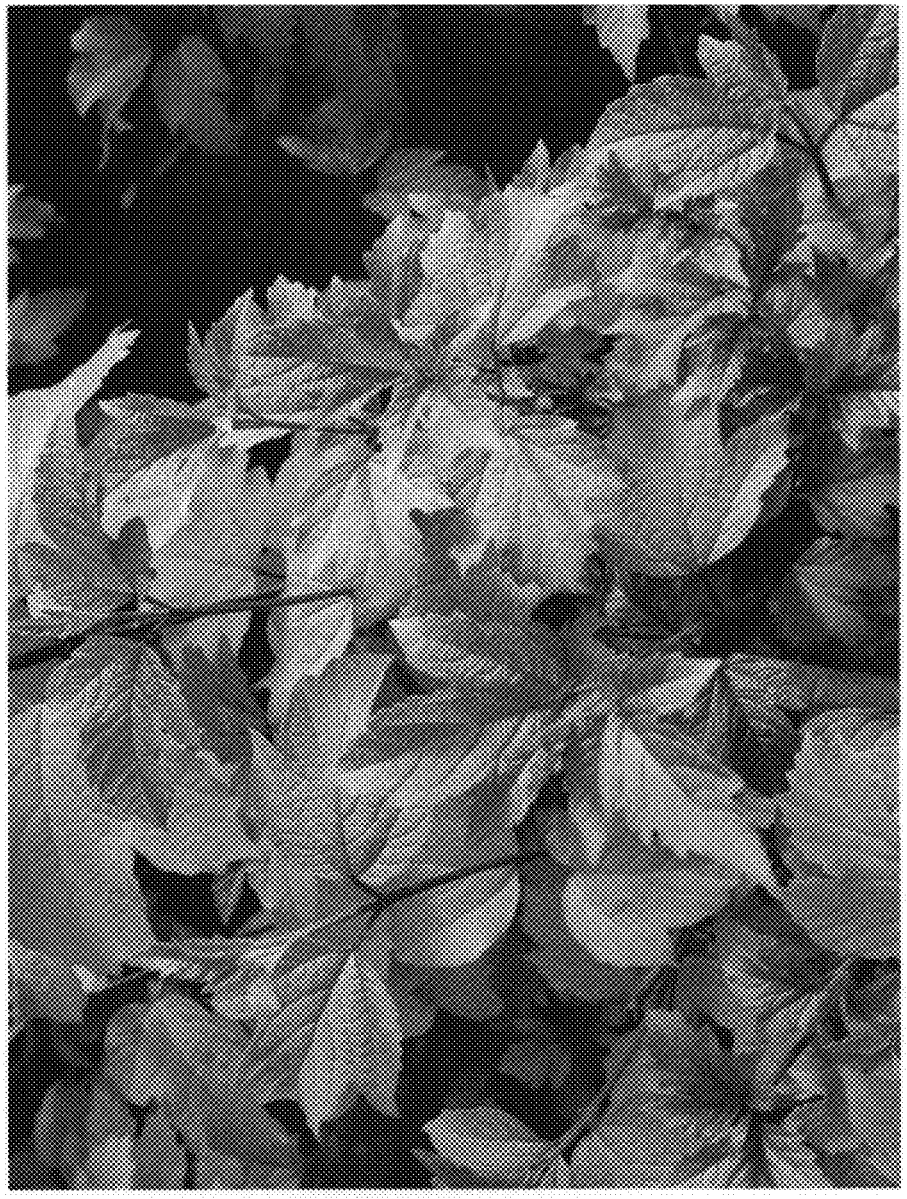

FIG. 3. Shows a close-up view of new foliage.

Figure 4:
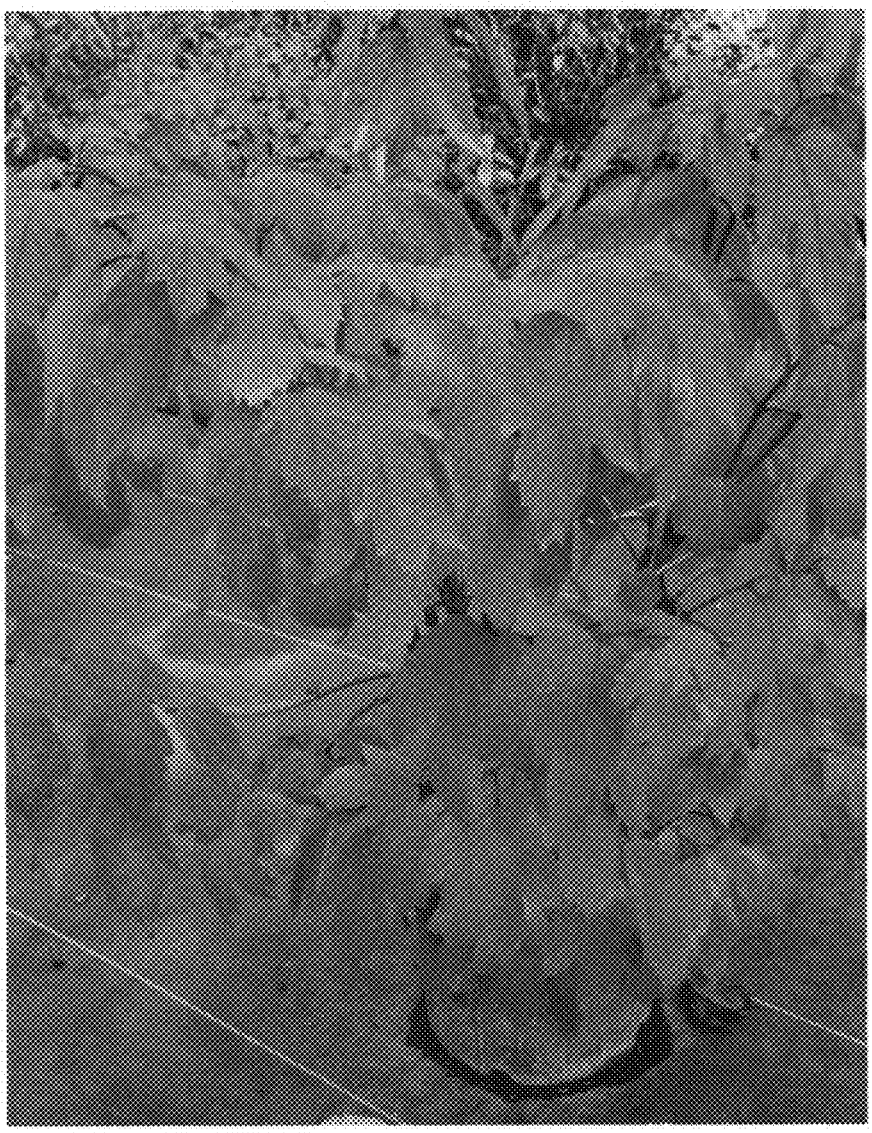
Figure 5:
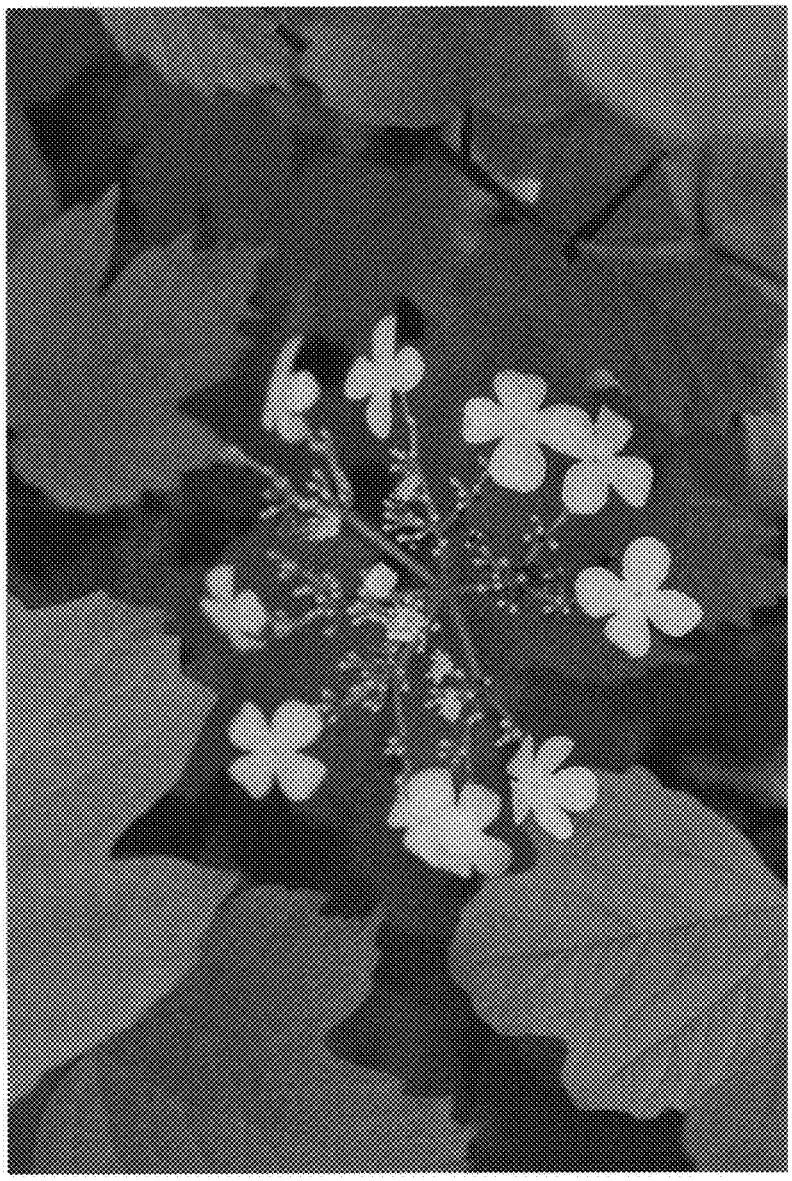
Figure 6:
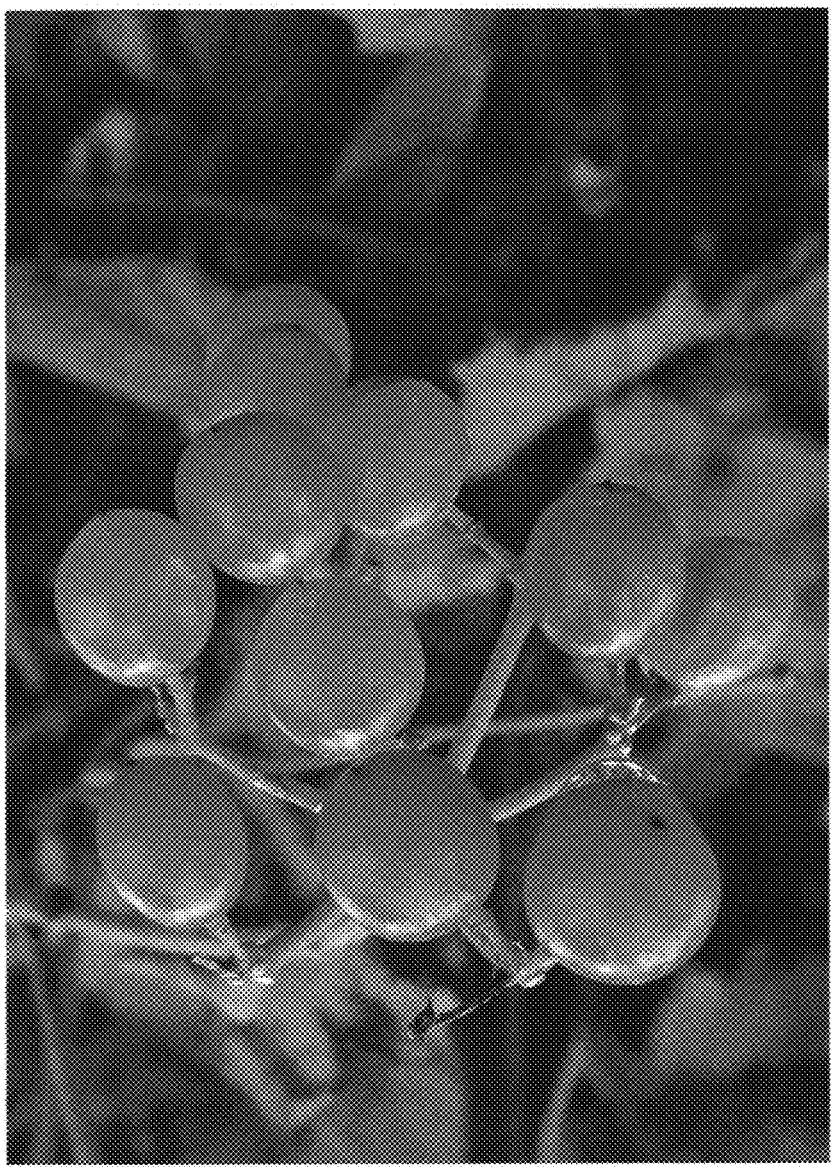

FIG. 4. Shows Fall foliage coloration.
FIG. 5. Shows a close-up view of the inflorescence.
FIG. 6. Shows a close-up view of the fruit.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNBDO' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Viburnum opulus* 'SMNVODR'.

Propagation:
- *Typical method*.—Softwood cuttings.
- *Time to initiate rooting*.—28 days at approximately 27° C.
- *Time to produce a rooted young plant*.—About 3 months at approximately 27° C.
- *Root description*.—Dense, free branching roots of moderate thickness. Colored yellow-white, not accurately measured with an R.H.S. chart.

Plant description:
- *Age of plant described*.—About 2.5 years in a 3 gallon container.
- *Growth habit*.—Perennial shrub. Full plant, upright and outwardly spreading.
- *Height*.—78 cm, unpruned.
- *Width*.—72 cm unpruned.
- *Growth rate*.—Moderate to fast.

Branches:
- *Branching habit*.—Free basal branching. Plants do not require pinching, but, typically pruned once during the Winter to develop a fuller plant.
- *Lateral branch quantity*.—Average 56.
- *Lateral branch length*.—Average range 55 to 68 cm.
- *Lateral branch diameter*.—Average 6 mm.
- *Branch angle*.—Typically acute angle from base, forming upright growth with a slight outward spread.
- *Branch strength*.—Strong, but, not flexible when bent.
- *Branch texture*.—Finely pubescent.
- *Branch color*.—Yellow-Green 152B, tips Greyed-Purple 183A.
- *Internode length*.—5 to 8 cm.

Foliage:
- *Leaves*.—Persistence: Semi-evergreen. Arrangement: Opposite, simple. Length: Avg. 11.5 cm. Width: Avg. 10.0 cm. Shape: Broad-ovate, trilobed. Apex: Acuminate. Base: Obtuse. Margin: Large serrations. Texture upper surface: Glabrous, plastic-like. Texture lower surface: Velvety, slightly pubescent. Color: Emerging leaves: Upper: Close to Greyed-Red 178A or Greyed-Orange 173A, with an overlay Yellow-Green N144B. Lower: Near Greyed-Orange 173A, with an overlay Yellow-Green N144B. Pubescence colored near N144C. Mature leaves during growing season: Upper: Near Yellow-Green N144C. Lower: Near Yellow-Green 145A. Venation: Grey-Purple (183C) to Yellow-Green (146D), both upper and lower sides. Texture: Upper side glossy and slightly pubescent; glabrous below. Fall foliage color: New Growth. Upper: Near R.H.S. Greyed-Purple 183B. Lower: Near R.H.S. Greyed-Purple 183B. Mature: Upper: Majority of leaves near Greyed-Red 179A, some foliage half 179A and half yellow 2B. Lower: Majority of leaves near Greyed-Red 179A, some foliage half 179A and half yellow 2B.
- *Venation*.—Palmate, color indistinguishable from leaf blade upper and lower surfaces.
- *Petiole*.—Length: Average range 1.5 to 2.5 cm. Width: Average 2.5 mm. Texture: Slightly pubescent, velvety or fuzzy. Color: New growth upper surface: Near Greyed-Orange 166A. New growth lower surface: Near Greyed-Red 178B. Mature growth both surfaces: Near Yellow-Green N144C.
- *Foliage durability*.—Good durability, strong performance in full sun.

Inflorescence:
- *Description*.—Terminal cyme. Lace cap.
- *Number of flowers per inflorescence*.—6 to 21 sterile, 300 to 400 fertile.
- *Flowering season*.—Late Spring to Summer.
- *Flower longevity*.—2-3 weeks.
- *Fragrance*.—Slightly sweet.
- *Inflorescence height*.—Avg. 9.0 cm.
- *Inflorescence diameter*.—Avg. 7.4 cm.
- *Flowers*.—
- *Flower diameter*.—Avg. 1.5 cm sterile flowers, Avg. 2 mm fertile flowers.
- *Flower depth*.—Avg. 2.5 cm sterile flowers Avg. 3 mm fertile flowers.
- *Flower bud*.—Length: Less than 2 mm. Diameter: Less than 2 mm. Shape: Round. Color: Ranging from Yellow-Green 145D to White 155B.
- *Petals sterile and fertile flowers*.—Number: 5. Length: Avg. 1.5 cm sterile flowers, Avg. 3 mm fertile flowers. Width: Avg. 5 mm sterile flower, 1 mm fertile flowers. Shape: Obovate. Apex: Obtuse. Base: Fused. Margin: Entire.
- *Texture*.—Glabrous, silky upper and lower surfaces. Color: Immature upper surface: White 155B. Immature lower surface: White 155B. Mature upper surface: White 155B. Mature lower surface: White 155B.
- *Sepals*.—Corolla not observed.
- *Peduncle*.—Length: Avg. 1.5 cm. Width: Avg. 2 mm. Color: Yellow-Green N144D. Texture: Glabrous. Angle: Approximately 30 degrees. Strength: Good.
- *Pedicels*.—Length: Avg. 2 mm. Diameter: Avg. 1 mm. Texture: Glabrous. Color: Yellow-Green N144D.

Reproductive organs:
- *Gynoecium*.—Pistil number: About 3. Pistil length: About 1 mm. Stigma shape: 3-lobed. Stigma color: White 155CB. Style length: Less than 1 mm. Style color: White 155CB.
- *Androecium*.—Stamen number: 5. Anther shape: Round. Anther length: 0.5 mm. Filament length: 1 mm. Filament color: Yellow-White 158C. Anther color: Yellow-White 158B. Amount of pollen: Scant. Pollen color: Yellow-White 158B.

Other characteristics:
- *Fruit*.—Approximately 10 to 20 fruits per inflorescence. Ovate drupe 9 mm long, 7 mm in diameter, colored Red 42A, smooth texture.

*Seed.*—1 seed per fruit. 7 mm long, 6 mm wide. Ovate, colored near Yellow-Orange 18B.

*Disease and insect resistance.*—No significant disease or pest resistance nor susceptibility have been observed.

*Cold hardiness.*—Observed to tolerate temperatures between −31° C. and 38° C.

What is claimed is:

1. A new and distinct *Viburnum* plant named 'SMN-VODR' as illustrated and described herein.

* * * * *